United States Patent [19]

Haschke et al.

[11] 3,984,341

[45] Oct. 5, 1976

[54] IODOPHORS AND A PROCESS FOR THEIR PREPARATION

[75] Inventors: Heinz Haschke; Gerhard Morlock, both of Hanau, Germany

[73] Assignee: Deutsche Gold-und Silber-Scheideanstalt vormals Roessler, Frankfurt am Main, Germany

[22] Filed: Jan. 13, 1975

[21] Appl. No.: 540,631

[30] Foreign Application Priority Data

Jan. 24, 1974 Germany.......................... 2403225

[52] U.S. Cl............................ 252/106; 260/67 UA; 260/29.6 H; 424/81; 424/150; 260/535 P; 260/535 H
[51] Int. Cl.²......................................... D11D 3/48
[58] Field of Search ............... 252/106; 424/78, 79, 424/81, 82, 150; 260/67 UA

[56] References Cited
UNITED STATES PATENTS

| | | | |
|---|---|---|---|
| 2,900,305 | 8/1959 | Siggin .............................. | 424/150 X |
| 2,987,505 | 6/1961 | Werner............................ | 260/77.5 |
| 3,028,300 | 4/1962 | Cantor et al....................... | 424/150 |
| 3,136,755 | 6/1964 | Grosser et al..................... | 260/239.3 |
| 3,150,096 | 9/1964 | Schmidt et al..................... | 252/106 |
| 3,367,877 | 2/1968 | Cantor et al....................... | 252/106 |
| 3,437,647 | 4/1969 | Freifeld............................. | 260/88.3 |
| 3,686,145 | 8/1972 | Haschke et al. ................... | 260/67 U |
| 3,793,222 | 2/1974 | Haschke et al. ................... | 252/180 |

*Primary Examiner*—P.E. Willis, Jr.
*Attorney, Agent, or Firm*—Beveridge, DeGrandi, Kline, Lunsford

[57] ABSTRACT

A non-foaming iodophor having a high content of active iodine comprises the product formed by mixing while heating at about 50°–120°C for about 0.75–15 hours a reaction mixture of:

I. about 10–30 weight percent of elementary iodine; and
II. about 90–70 weight percent of an aqueous solution consisting essentially of:
  a. about 7–30 weight percent of at least one polycarboxylic acid, at least one polycarboxylate or mixtures of said polycarboxylic acids and polycarboxylates, having at least 65 carboxyl or carboxylate groups per 100 monomer units in the polymer chain and an average degree of polymerization (numerical average value) between about 10 and 500;
  b. about 0–20 weight percent of at least one alkali metal iodide, ammonium iodide, mixtures of said iodides or at least one lower, monovalent, aliphatic alcohol;
  c. about 0–20 weight percent of at least one non-volatile multibasic mineral acid, at least one multibasic oxycarboxylic acid, or mixtures of said acids, wherein said acids do not substantially reduce elementary iodine; and
  d. water in an amount sufficient so that said aqueous solution comprises 100 weight-percent. The iodophor exhibits biocidal activity.

23 Claims, No Drawings

IODOPHORS AND A PROCESS FOR THEIR PREPARATION

This invention relates to aqueous solutions of complex iodine compounds and a process for their preparation. More particularly, this invention relates to non-foaming iodophors having favorable proportions of active and inactive iodine.

Iodophors are aqueous solutions of complex iodine compounds, which are suitable as disinfecting agents. Iodophors do not exhibit or exhibit to only a small extent the disagreeable characteristics of free iodine, namely: its low water solubility, its high vapor pressure even at a relatively low temperature, its high degree of corrosiveness and its highly irritating odor (cf. F. Suntrup: Brauwelt 107, No: 40 (1967), pp. 760 to 766; R. S. White: Am. Soc. of Brewing Chemists, Proc. Congr. 1965, pp. 84 to 89; and A. M. Upperton: Wallerstein Communications XXVIII, No: 96 (1965), pp. 137 to 141).

Iodophors based on polyvinylpyrrolidone are known in the art (c.f. U.S. Pat. No. 2,706,701). Such iodophors, however, have the disadvantage that they only have a limited compatibility with acids. The microbiocidal effect of iodine is, however, particularly marked especially in an acid medium and drops off considerably in an alkaline medium. Also the proportion of available to inactive iodine is only about 2:1, which corresponds merely to about 67% utilization of the iodine. Beyond that the water solubility and especially the possibility of dilution in water leaves much to be desired.

Furthermore, iodophors based on tensides are also known in the art (cf. R. S. White, loc. cit.). In these iodophors the proportion of available to inactive iodine is generally somewhat more favorable than in the case of the polyvinylpyrolidone iodophors. However, because of their strong inclination to foaming they are unsuitable for many industrial purposes where the development of foam is not desired, for example in nozzle cleaning installations in breweries. Therefore, they are rarely used despite their particularly easy washability.

There exists a need in the art for an iodophor and a process for its preparation wherein the iodophor has a high proportion of active iodine relative to inactive iodine, good compatibility with acids, good water solubility and non-foaming properties, and improved biocidal action, and good stability over time, while retaining the heretofore known advantages of iodophors. This invention aids in fulfilling these needs.

This invention provides a process for the production of non-foaming iodophors having a high content of active iodine. The process comprises mixing while heating a mixture of:

I. about 10–30 weight percent of elementary iodine; and
II. about 90–70 weight percent of an aqueous solution consisting essentially of:
   a. about 7–30 weight percent of at least one polycarboxylic acid, at least one polycarboxylate or mixtures of said polycarboxylic acids and polycarboxylates, having at least 65 carboxyl or carboxylate groups per 100 monomer units in the polymer chain and an average degree of polymerization (numerical average value) between about 10 and 500;
   b. about 0–20 weight percent of at least one alkali metal iodide, ammonium iodide, mixtures of said iodides or at least one lower, monovalent, aliphatic alcohol;
   c. about 0–20 weight percent of at least one non-volatile multibasic mineral acid, at least one multibasic oxycarboxylic acid, or mixtures of said acids, which do not substantially reduce elementary iodine; and
   d. water in an amount sufficient so that said aqueous solution comprises 100 weight-percent.

The heating is conducted at between about 50° and 120°C for about 0.75 to 15 hours with good intermixing to form the iodophor. Unreacted iodine, if any, can subsequently be separated. This invention also provides iodophors prepared by the process of this invention.

Additionally, this invention provides the iodophor of this invention having uniformly dissolved therein up to about 3 weight percent of at least one non-ionic surfactant, related to the weight of the iodophor.

As a result of the process of the invention, iodophors can be produced which are free of nitrogen, do not foam and have a more favorable proportion of active (i.e., titratable with thiosulfate) iodine to inactive iodine than all hitherto known iodophors. Beyond that, the iodophors of this invention based on polycarboxylates show an improved biocidal effect as compared with known iodophors having the same content of active iodine.

Polyacrylic acids, poly ($\alpha$-hydroxy acrylic acids), homo or copolymerizates of maleic acid or of other unsaturated dicarboxylic acids, such as itaconic acid, or the corresponding alkali metal salts are suited as the polycarboxylic acids solubilizing elementary iodine. The polycarboxylic acids or polycarboxylates must have a content of carboxyl or carboxylate groups of at least about 65 basic mole % (i.e., at least about 65 carboxyl or carboxylate groups per 100 monomer units in the polymer chain; cf. E. Trommsdorff, Inaugural Dissertation, Freiburg i. Br., 1931) and an average degree of polymerization ($\overline{P}$; numerical average value) between about 10 and about 500.

It is particularly advantageous to employ as solubilizers such polycarboxylates that contain carbonyl and/or hydroxyl groups in addition to the predominant number of carboxyl or carboxylate groups. These polycarboxylates, depending on which of the mentioned groups they contain in what proportion, are called poly (aldehydo carboxylates) — for short PAC —, poly (hydroxycarboxylates) — for short POC —, or poly (hydroxyaldehydo carboxylates) — for short PAoC or POaC, depending on their predominant character. The average degree of polymerization ("viscosity-average-value" corresponding by calibration to the average) number of monomer units in the polycarboxylate molecule chain) of the representatives of this polycarboxylate group, suitable for the process of the invention, are between about 10 and about 500, preferably between about 10 and about 300, especially between about 15 and about 100. The data related to the average degree of polymerization are to be understood in such a way that their values of 10, 15, 100, 300 or 500, correspond to values of the reduced viscosity, measured on 1% solutions of free poly (aldehydo carboxylic acids), or for the poly (hydroxycarboxylates) and the poly (hydroxyaldehydo carboxylates) measured on the poly (aldehydo carboxylic acids) constituting the base of the former as intermediate products, of 0.047, 0.053, 0.095, 0.200 or 0.300 deciliters per gram, respectively, whereby the free poly (aldehydo carboxylic acids) for the preparation of 1% poly (aldehydo carboxylic acid) solutions required for measurement are doused first with corresponding quantities of 5% aqueous $SO_2$ solutions, and then after complete dissolution has occurred, refilled with an equal volume of 10% aqueous NaCl solution. The viscosimetric masurement is made at 20°C.

Such polycarboxylates are built up from:
Y + W/2 basic mole % units of the general formula

U — W basic mole % units of the general formula

Z basic mole % units of the general formula

W/2 basic mole % units of the general formula

V basic mole % units of the general formula

wherein U equals about 5 to about 30; V equals about 1 to about 25, preferably about 1 to about 15, especially about 1 to about 10; W equals 0 to U, preferably 0 to 0.3·U, especially 0; Y equals .100 − (U + V + Z) and Z equals 0 to about 20, preferably 0 to about 10, especially 0; A represents an alkali metal or hydrogen ion, preferably a hydrogen ion; $R_1$ signifies hydrogen, methyl, hydroxymethyl, ethyl, chlorine or bromine, preferably hydrogen or hydroxymethyl, especially hydrogen; $R_2$ and $R_4$ are the same or different and signify hydrogen or hydroxymethyl, preferably hydrogen; $R_3$ and $R_5$ are the same or different and signify hydrogen, methyl or ethyl, preferably hydrogen; and whereby it must be met as a marginal condition that the expression Y + (W/2) + 2Z is larger than or equal to 65.

Accordingly, the free poly (aldehydo carboxylic acids) are particularly suited for the production of the iodophors of this invention. The portions of the units with the general formulas (I) to (V) are stated in basic mole % according to E. Trommsdorff, i.e., as the average number of the pertinent formula units per all together 100 formula units (I) to (V) in the polymer molecules.

The poly (aldehydo carboxylates), poly (hydroxycarboxylates) and poly (hydroxy aldehydo carboxylates), defined before, as well as suitable processes for their production have been described in detail in the German application Ser. Nos. 1,904,940; 1,904,941 and 1,942,556, opened to publ. insp., as well as in the Austrian patents 313,235; 313,577 and 306,681. They are, among others, eminently suitable as complex builders in cleaning, degreasing and rust preventing agents. Whenever they are employed as solubilizers in the production of iodophors of this invention, they also impart an additional higher stability vis-a-vis hard water as well as a certain dirt-bearing capactiy to the iodophors.

The solubilizing effect of the polycarboxylic acids or polycarboxylates can even be considerably increased by the simultaneous use of suitable "co-solubilizers." Especially the alkali metal iodides and ammonium iodide come into consideration as such. Sodium iodide and ammonium iodide are especially preferred. Other suitable "co-solubilizers" are lower monovalent aliphatic alcohols, such as $C_1$–$C_6$ alkyl alcohols, e.g. methanol, ethanol, propanol and isopropyl alcohol. The mentioned solubilizers, together with the polycarboxylic acids or polycarboxylates clearly produce synergistic effects. Lastly, mixtures of alkali metal iodides or ammonium iodide with the mentioned alcohols can also be employed as co-solubilizers. Synergistic effects in case of the simultaneous use of such mixtures and of the polycarboxylic acids or polycarboxylates will, to be sure, result only whenever the content of the mixtures of the mentioned iodides amounts to below about 40 or above about 95% by weight.

Since the microbicidal effect of the iodine is particularly marked in an acid medium, suitable acids are advantageously added during the production of the iodophors. Such acids are non-volatile, multibasic mineral acids that do not reduce elementary iodine, such as sulfuric acid or preferably phosphoric acid. Also non-volatile, multi-basic oxycarboxylic acids that do not reduce elementary iodine, such as citric acid, malic acid or tartaric acid, can be used to advantage. By non-volatile is meant that the acids do not substantially volatilize during the preparation or use of the iodophors of this invention.

The process of this invention is carried out in such a way that a mixture of about 10 to about 30% by weight, preferably about 20 to about 30% by weight of elementary iodine with about 90 to about 70% by weight, preferably about 80 to about 70% by weight of an aqueous solution of the remaining components, with good intermixing, e.g., in a vessel equipped with an agitator or in a circulation reactor, is heated to a temperature between about 50° and about 120°C until the iodine is largely or completely dissolved. Whenever temperatures above about 70°C are employed, then the use of a closed pressure vessel is recommended. Generally the dissolution of the iodine requires from about 0.75 to about 15 hours, especially from about 1 to about 10 hours. Insofar as undissolved iodine is still present after the solution process, it is separated, such as by filtration or centrifuging. Recovered iodine can be reused directly just like the iodine possibly sublimated off during the dissolution process.

The aqueous solution employed during production of the iodophors consists essentially of about 7 to about 30% by weight, preferably about 15 to about 25% by weight of the polycarboxylic acids and polycarboxylates described in more detail farther back. In addition, it can contain up to about 20% by weight, preferably up to about 15% by weight, especially about 7 to about 11% by weight of at least one alkali metal iodide and/or ammonium iodide or equal quantities by weight of saturated low, monovalent, aliphatic alcohols having 1 to 3 carbon atoms, and up to about 20% by weight, preferably about 3 to about 15% by weight, especially about 7 to about 11% by weight of the acids described in more detail above. The remainder is water.

As a result of the process of this invention, iodophors having a content of about 7 to about 26% by weight of active iodine can be produced. The weight ratio of active iodine contained dissolved in the iodophor and formed from the elementary iodine used, to dissolved, inactive iodine formed in the iodophors of this invention varies between about 16:1 and about 2:1.

The iodophors produced according to the process of this invention can be diluted with water for practical use, as desired, without any separation or formation of precipitate occurring. They show no tenside activity whatever; a 1% by weight solution in distilled water, after 30 seconds of intensive shaking shows no stable foam whatever. The "foam phase" rather collapses within fewer than 30 seconds, therefore about just as fast as with pure water.

Applied dilute solutions throughout show a higher microbicidal action than do solutions of known iodophors having the same content of active iodine.

The absolutely non-tensidic iodophors based on the polycarboxylates are particularly well suited for numerous practical uses, especially in the brewery business, precisely because of their lack of any kind of tenside characteristic. Moreover they inherently exhibit a certain cleaning effect because of their content of polycarboxylates acting as dispersing agents and as carriers of dirt. If, however, it is desired in certain cases to achieve a tensidic effect at the same time, then an addition of suitable tensides is also possible. They can be added to the iodophors in quantities up to about 3% by weight, related to the weight of the iodophor.

EXAMPLES

In the following examples the following polycarboxylic acids and polycarboxylates are used. All parts, proportions, percentages and ratios are by weight unless otherwise indicated.

Poly(aldehydo carboxylic acid)A

A poly(aldehydo carboxylic acid)-solution was produced by oxidative copolymerization of 20 mole % acrylic acid with 80 mole % of acrolein in aqueous, 20% by weight hydrogen peroxide at 70°C (1.1 mole acrolein per mole $H_2O_2$; dosing in of the monomer mix to the stirred hydrogen peroxide within 4 hours). After distillative separation of the most part of the residual monomers, there remained a 35% by weight solution of a poly(aldehydo carboxylic acid) which is characterized by the following parameters:

$Y = 70$ basic mole %, $U = 17$ basic mole %, $V = 13$ basic mole %, $W = 0$ basic mole %, $Z = 0$ basic mole %; with an average degree of polymerization ("viscosity average value") of $\bar{P} = 20$.

Poly(hydroxycarboxylate)B

The previously described poly(aldehydo carboxylic acid)A solution was neutralized by dosing in of a 40% by weight caustic soda solution at 35°C and by further addition of the caustic soda solution was subjected to the Cannizzaro reaction at a pH = 12. After neutralization of the alkaline reaction mix with a portion of the poly(aldehydo carboxylic acid)A solution to pH 7, a 36% by weight aqueous solution of a poly (hydroxycarboxylate) was obtained which is characterized by the following parameters:

$Y = 70$ basic mole %, $U = 17$ basic mole %, $V = 13$ basic mole %, $W = 16$ basic mole %, $Z = 0$ basic mole %; with an average degree of polymerization (viscosity average value) of $\bar{P} = 20$. From these data the equivalent weight of the POCNa salt (considering the degree of neutralization of 0.88 as it exists at an adjustment to pH 7, and considering the analytically determinable terminal groups) was: 109.0.

Poly(aldehydo carboxylic acid)C

By oxidative copolymerization of 50 mole % acrylic acid with 50 mole % acrolein in aqueous, 20% by weight hydrogen peroxide at 70°C (1.1 mole acrolein per mole $H_2O_2$; dosing in of the monomer mix to the stirred hydrogen peroxide mix within 4 hours) a poly-(aldehydo carboxylic acid) solution was produced. After distillative separation of the most part of residual monomers, there remained a 32.5% by weight solution of a poly(aldehydo carboxylic acid), which is characterized by the following parameters:

$Y = 78$ basic mole %, $U = 16$ basic mole %, $V = 6$ basic mole %, $W = 0$ basic mole %, $Z = 0$ basic mole %, with an average degree of polymerization ("viscosity average value") of $\bar{P} = 60$.

Poly(aldehydo carboxylate)D

The previously described poly(aldehydo carboxylic acid)C solution was neutralized by dosing in of 45% by weight of caustic soda solution at 35°C to pH 7. An about 37% by weight solution of the poly(aldehydo carboxylate) developed. The equivalent weight of this PAC Na salt (considering the degree of neutralization of 0.88 as it exists in case of adjustment of pH 7 and considering the analytically determinable terminal groups) amounted to: 107.7.

Poly(hydroxycarboxylate)E

By further addition of caustic soda solution to the previously described poly(aldehydo carboxylate)D solution up to pH 12, a Cannizzaro reaction was conducted. After neutralization of the alkaline reaction mixture with a portion of the poly(aldehydo) carboxylic acid)C solution to pH 7, a 38% by weight, aqueous solution of a poly(hydroxycarboxylate) was obtained which is characterized by the following parameters:

$Y = 78$ basic mole %, $U = 16$ basic mole %, $V = 6$ basic mole %, $W = 15$ basic mole %, $Z = 0$ basic mole %; with an average polymerization degree ("viscosity average value") of $\bar{P} = 60$. From these data, there results an equivalent weight (considering the degree of neutralization of 0.88 as it exists in case of adjustment of pH 7 and considering the analytically determinable of: 101.5.

Poly(hydroxycarboxylate)F

The just described solution of the poly(aldehydo carboxylic acid)C was neutralized with 45% by weight caustic soda solution exactly as described in case of the further processing to the poly(aldehydo carboxylate)D and the poly(hydroxycarboxylate)E and was reacted according to Cannizzaro, with this difference that the entire neutralization and Cannizzaro reaction was carried out in the pesence of 1.5 moles formaldehyde (added as a 40% formalin solution) per mole aldehyde groups in the poly(aldehydo carboxylic acid) solution. The poly(hydroxycarboxylate) obtained after neutralization of the alkaline reaction mixture with a portion of poly(aldehydo carboxylic acid) solution to pH 7 (obtained as 34% by weight aqueous solution) is characterized by the following parameters:

$Y = 78$ basic mole %, $U = 16$ basic mole %, $V = 6$ basic mole %, $W = 13$ basic mole %, $Z = 0$ basic mole %; with an average degree of polymerization ("viscosity average value") of $P = 60$. The structure of this poly(hydroxycarboxylate) corresponded to the following, summary, simplified approximate formula, not considering the sequences of formula units (to be assumed as statistical):

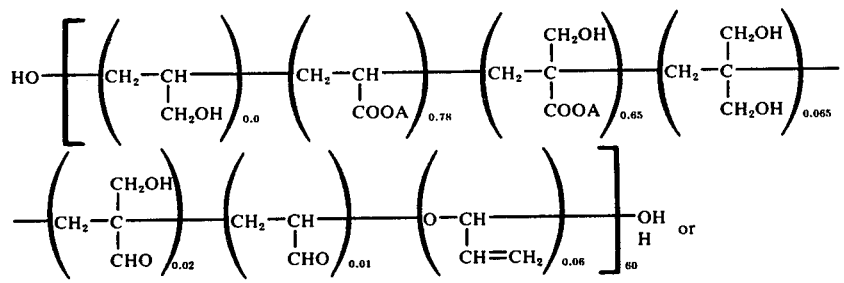

where A signifies Na or H, i.e., corresponding to the apparent dissociation constant of this poly(hydroxycarboxylic acid) compound [or of the basis free poly(hydroxycarboxylic acid)] and corresponding to the pH adjustment of the poly(hydroxycarboxylate) solution to pH 7; A signifies 0.88 Na ions per 0.12 H ions. The equivalent weight of this compound, considering the degree of neutralization of 0.88 and considering the degree of neutralization of 0.88 and considering the analytically determinable terminal groups, therefore, is: 107.6.

Poly(hydroxycarboxylate)G

A poly(aldehydo carboxylic acid) solution was produced by oxidative copolymerization of 65 mole % of acrylic acid with 35 mole % acrolein in aqueous, 20% by weight hydrogen peroxide at 60°C (1.1 moles $H_2O_2$ per mole acrolein, dosing in of the monomer mix to the stirred hydrogen peroxide within 4 hours). In order to maintain the reaction mixture well stirrable, it was diluted with water toward the end of the dosing-in of monomer. After 12 hours of reacting of the reaction mixture, 20 volume % of the reaction mixture were distilled off in a vacuum (100 torr). As a result of that, the remainder of unreacted monomers was practically completely eliminated. By careful neutralization and alkalization with 45% by weight of caustic soda solution while cooling to temperatures below 40°C the copolymerizate was reacted according to Cannizarro. After neutralization of the excess alkali with 65% by weight of phosphoric acid a 37% by weight aqueous solution of a poly(hydroxycarboxylate)containing small quantities of sodium phosphate, was obtained, which is characterized by the following parameters:

$Y = 85$ basic mole %, $U = 14$ basic mole %, $V = 1$ basic mole %, $W = 12$ basic mole %, $Z = 0$ basic mole %, with an average degree of polymerization ("viscosity-average value") of $\bar{P} = 120$.

Polycarboxylic acid H

According to the process described in the German published application No. 2,032,953, a mixture of 200 ml n-heptane and 100 ml decalin, containing 0.17g of benzoyl peroxide was prepared in a 1-liter quick-fit, wide necked flask, equipped with a paddle agitator, a reflux cooler, thermometer and drop-in measure. This preparation, while stirring violently (300 rpm), was kept in an oil bath (140°C) at a high reflux (boiling point 110°C). Immediately after reaching the boiling point of the preparation, addition was started of a solution consisting of 60 ml freshly distilled acrylic acid, 0.34 g of benzoylperoxide, 0.025 g of hydroquinone, 0.06 g of freshly distilled vinyl acetate, 132 ml of n-heptane and 68 ml of decalin from the drop-in measure at an addition rate of 52 ml/10 minutes. Ten minutes after the beginning of dosing-in, the first formation of acrylic acid bead polymerizate could be observed. At the end of the addition of monomer, stirring was continued for 10 minutes under reflux. Subsequently the polymerizate formed was filtered off and washed with n-heptane until the odor of the acrylic acid disappeared. After drying in a vacuum at 120°C, 58 g bead polyacrylic acid (bead diameter about 1 mm) were obtained. The polymerizate had an average degree of polymerization of 490.

EXAMPLE 1

17 g of poly(hydroxycarboxylate)F in form of a 40% by weight aqueous solution, 26 g elementary iodine (flakes) and sufficient distilled water to total 100 g were put in succession into a 100 ml round flask, equipped with a mechanical stirrer and a reflux cooler. The mixture was kept for 3 hours in a heated bath while stirring at 50°C. After cooling, the mixture was centrifuged for separation of undissolved iodine. A nonfoaming iodophor having a content of 15% by weight of active (i.e., titratable with thiosulfate) iodine and a density of 1.30 g cm$^{-3}$ in form of a free flowable liquid was obtained, which even after a week of storage at ambient temperature was still absolutely stable, and which could be diluted at random in water without precipitation of iodine.

EXAMPLE 2

17 g poly(aldehydo carboxylate)D in form of a 35% by weight aqueous solution, 26 g elementary iodine (as flakes) and distilled water were put in succession to total 100 g into a 100 ml round flask, equipped with a mechanical agitator and reflux cooler. The mixture was kept at 50°C in a heated bath for three hours while stirring and subsequently was centrifuged after cooling for separation of the undissolved iodine. A non-foaming iodophor with an 11.5% by weight content of active (i.e. titratable with thiosulfate) iodine and with a density of 1.27 g cm$^{-3}$ in the form of a free flowable liquid was obtained, which was still absolutely stable even after one week of storage at ambient temperature, and which could be diluted at random with water without precipitation of iodine.

EXAMPLE 3

17 g polycarboxylic acid H in form of a 40% by weight aqueous solution, 26 g elementary iodine (as flakes) and distilled water to 100 g were put in succession into a 100 ml round flask, equipped with mechanical stirrer and reflux cooler. The mixture was kept for 3 hours, while stirring, in a heated bath at 50°C, and subsequently after cooling it was centrifuged in order to separate undissolved iodine. A non-foaming iodophor with a 7% by weight content of active iodine (i.e. titratable with thiosulfate) and a density of 1.18 g cm$^{-3}$ in form of a free flowable liquid was obtained, which was still absolutely stable even after one week storage at ambient temperature and could be diluted arbitrarily with water without precipitation of iodine.

EXAMPLE 4

A mixture consisting of 16.8 g of poly(aldehydo carboxylic acid)A in form of a 35% by weight aqueous solution, 9 g of sodium iodide, 12.1 g of 65% by weight phosphoric acid and 5 ml distilled water were put in a 100 ml round flask, equipped with mechanical stirrer and reflux cooler. After adding 26 g of elementary iodine (as flakes) the mixture was kept for 2 hours in a heated bath at 60°C while stirring. After cooling and centrifuging away the undissolved iodine, a non-foaming iodophor having a 23% by weight content of active iodine (i.e. titratable with thiosulfate) and a density of 1.5 g cm$^{-3}$ in form of a free flowable liquid was obtained. On the basis of the determination of the portion of iodine used, which had been converted during the iodophor production into inactive iodine, a proportion of active to inactive iodine of 15.2:1 resulted for this iodophor. Even after 40 days of storage at ambient temperature the iodophor was still absolutely stable and could be arbitrarily diluted with water without precipitation of iodine.

EXAMPLE 5

According to a process, analogous to that described in Example 4, but with the use of the poly(aldehydo carboxylic acid) C instead of the poly(aldehydo carboxylic acid)A as stabilizer, a non-foaming iodophor with a content of active (i.e. titratable with thiosulfate) iodine of 20% by weight and a density of 142 g cm$^{-3}$ in form of an easy flowing liquid was obtained. On the basis of the determination of the proportion of iodine used, which during iodophor production had been converted into inactive iodine, a ratio of active to inactive iodine of 9.3:1 resulted for this iodophor. The iodophor was still absolutely stable even after a 40 day storage at ambient temperature and could be diluted at will with water without precipitation of iodine.

COMPARATIVE EXPERIMENT

Analogously to the process described in the preceding Examples, a mixture of 16.8% by weight of commercial polyvinyl pyrrolidone (average molecular weight = 25,000 − 30,000), 7.9% by weight of phosphoric acid (added in the form of 12.1 g of 65% by weight $H_3PO_4$ to 100 g mixture), 26% (26 g) elementary iodine and 49.3% of water were put in a 100 ml round flask, which was equipped with a mechanical stirrer and a reflux cooler and kept for 3 hours while stirring vigorously in a heated bath at 60°C.

Already after 1.5 hours there developed from the mixture a paste which could only be stirred with great difficulty. A sample of it, after centrifuging away the undissolved iodine had an iodine content of only 1.5% by weight. After 3 hours this was centrifuged again at 60°C after the cooling of the undissolved iodine. An iodophor was obtained, which in the form of a thick paste contained only 1.7% by weight of active (i.e. titratable with thiosulfate) iodine and from which during dilution with water, elementary iodine was precipitated.

EXAMPLE 6

A mixture of 16.8 % by weight of poly(aldehydo carboxylic acid)A, used as a 35% by weight aqueous solution, 1.8% by weight of sodium iodide, 12.1% by weight of 65% by weight phosphoric acid, 26% by weight of elementary iodine (as flakes) and the remainder distilled water to total 100%, was maintained in a 100 ml round flask while stirring (reflux cooler) for 3 hours at 60°C. After cooling and centrifuging away of the undissolved iodine, a non-foaming iodophor with a content of active (i.e. titratable with thiosulfate) iodine of 16.5% by weight and a density of 1.34 g cm$^{-3}$ in the form of a free flowing liquid was obtained. The iodophor remained still absolutely stable even after 40 days of storage at ambient temperature and could be diluted at will with water.

EXAMPLE 7

A mixture of 5% by weight poly(hydroxycarboxylate)B, 25% by weight of elementary iodine (as flakes), 5% by weight of citric acid and the remainder distilled water to total 100% were kept at 60°C for 3 hours while stirring and reflux cooling. After cooling and centrifuging away the undissolved iodine, a non-foaming iodophor with a content of active (i.e. titratable with thiosulfate) iodine of 7.8% by weight density a dnesity of 1.15 g cm$^{-3}$ in the form of a free flowing liquid was obtained. The iodophor was still absolutely stable even after 40 days of storage at ambient temperature and could be diluted at will with water.

EXAMPLE 8

A mixture of 5% by weight of poly(hydroxycarboxylate)B, 25% by weight of elementary iodine (as flakes), 10% by weight of citric acid, 7% by weight of ammonium iodide and the remainder distilled water to total 100%, was kept for 3 hours at 60°C in a 100 ml round flask while stirring and with reflux cooling. After cooling and centrifuging away the undissolved iodine, a non-foaming iodophor having a content of active (titratable with thiosulfate) iodine of 18.5% by weight and a density of 1.4 g cm$^{-3}$, in the form of a free flowing liquid was obtained. Even after 20 days of storage at ambient temperature and subsequently in the refrigerator at 0°C the iodophor was absolutely stable and it could be diluted with water at will.

EXAMPLE 9

A mixture of 8 g poly(hydroxycaboxylate)E and 8.8g poly(aldehydo carboxylic acid)A (the latter used as 35% by weight aqueous solution), 26 g elementary iodine, 9 g potassium iodide, 12.1 g of 65% by weight of phosphoric acid and sufficient distilled water to total 100 g, was kept for 45 minutes at 60°C while stirring and with reflux cooling in a 100 ml round flask. After cooling and centrifuging away of the undissolved iodine, a non-foaming iodophor having a content of 24% by weight of active (i.e. titratable with thiosulfate) iodine and a density of 1.52 g cm$^{-3}$ was obtained in form on a free flowing liquid. The iodophor was still absolutely stable even after 36 days of storage at ambient temperature and could be diluted at will with water.

EXAMPLE 10

A mixture of 10 g poly(aldehydo carboxylic acid)A and 7 g of poly(hydroxycarboxylate)G (the polycarboxylic acid was used as a 35% by weight, aqueous solution), 26 g of elementary iodine, 9 g of sodium iodide, 12.1 g of 65% by weight of phophoric acid and sufficient distilled water to total 100 g was kept in an autoclave with even intermixing (magnetic mixer operated from the outside) for 2 hours at 120°C. After cooling and centrifuging away the undissolved iodine a non-foaming iodophor with a content of 25% by weight of active (i.e. titratable with thiosulfate) iodine and a density of 1.53 g cm$^{-3}$ in form of a free flowing liquid was obtained. The iodophor was still abolutely stable even after 36 days of storage at ambient temperature and could be diluted at will with water.

EXAMPLE 11

A mix of 15 g poly(aldehydo carboxylic acid)A (used in the form of a 35% by weight, aqueous solution), 26 g of elementary iodine, 12 g of 65% by weight of phosphoric acid and sufficient distilled water to total 100 g was kept in a 100 ml round flask for 15 hours at 60°C while stirring. After cooling and centrifuging away the undissolved iodine, a non-foaming iodophor with a content of active (i.e. titratable with thiosulfate) iodine of 16% by weight and a density of 1.3 g cm$^{-3}$, in the form of a free flowing liquid was obtained. The iodophor was absolutely stable, even after a 36 day storage at ambient temperature and could be diluted at will with water.

It will be apparaent from the foregoing disclosure that this invention is accompanied by many disadvantages. The iodophor of this invention has a high proportion of active iodine relative to inactive iodine and has very high microbiocidal activity. The iodophor is compatible with acids and exhibits excellent water solubility. It is substantially non-foaming. The iodophor is very stable (e.g. iodine does not precipitate) over periods of time, even after storage at relatively low temperatures. The iodophor of this invention can be prepared in the form of a free flowing liquid; upon dilution with water elementary iodine does not readily precipitate.

What is claimed is:

1. A process for the production of an iodophor, said process comprising mixing while heating a mixture of:
   I. about 10–30 weight percent of elementary iodine; and
   II. about 90–70 weight percent of an aqueous solution consisting essentially of:
      a. about 7–30 weight percent of at least one polycarboxylate having an average degree of polymerization (numerical average value) between about 10 and 500, said polycarboxylate consisting essentially of:

Y + W/2 basic mole % units of the formula

U – W basic mole % units of the formula

Z basic mole % units of the formula

W/2 basic mole % units of the formula

V basic mole % units of the formula

wherein U equals about 5–30; V equals about 1–25; W equals 0 to U; Y equals 100 – (U + V + Z); and Z equals 0 to 20; A represents an alkali metal or hydrogen ion; $R_1$ signifies hydrogen, methyl, hydroxy methyl, ethyl, chlorine or bromine; $R_2$ and $R_4$ are the same or different and signify hydrogen or hydroxymethyl; $R_3$ and $R_5$ are the same or different and signify hydrogen, methyl or ethyl; and whereby the expression Y+(W/2)+2Z is larger than or equal to about 65;
      b. about 0–20 weight percent of at least one alkali metal iodide, ammonium iodide, mixtures of said iodides or at least one lower, monovalent, aliphatic alcohol;
      c. about 0–20 weight percent of at least one acid selected from the group consisting of sulfuric acid, phosphoric acid, citric acid, malic acid and tartaric acid; and
      d. water in an amount sufficient so that said aqueous solution comprises 100 weight percent;

wherein said heating is conducted at between about 50° and 120°C for a period of time sufficient to form said iodophor.

2. Process according to claim 1 wherein undissolved iodine remains at the end of the reaction and said iodine is separated from said iodophor.

3. Process according to claim 1 in which said reaction mixture is heated at a temperature above about 70°C in a closed pressure vessel.

4. Process according to claim 1 wherein said reaction mixture comprises:
   I. about 20-30 weight percent of elementary iodine; and
   II. about 80-70 weight percent of said aqueous solution.

5. Process according to claim 1 wherein component (a) is about 15-25 weight percent.

6. Process according to claim 1 wherein component (b) comprises about 7-11 weight percent of an alkali metal iodide, ammonium iodide or a mixture of said iodides.

7. Process according to claim 1 wherein component (c) is about 7-11 weight percent.

8. Process according to claim 1 wherein said polycarboxylate has an average degree of polymerization of about 10-300.

9. Process according to claim 8 wherein said average degree of polymerization is about 15-100.

10. Process according to claim 1 wherein V equals about 1-15; W equals 0 to about 0.3 U; Z equals 0 to about 10; A represents a hydrogen ion; $R_1$ and Ru signifies hydrogen or hydroxy methyl; $R_2$, $R_3$ and $R_5$ are each hydrogen.

11. Process according to claim 10 wherein V equals about 1-10; W equals 0; Z equals 0; and $R_1$ signifies hydrogen.

12. Process according to claim 6 wherein said alkali metal iodide is sodium iodide.

13. Process according to claim 1 wherein said alcohol is a $C_1$-$C_3$ saturated, monovalent, aliphatic alcohol.

14. Process according to claim 1 wherein said heating and mixing are conducted for about 1-10 hours.

15. An iodophor comprising the product formed by mixing while heating a mixture of:
   I. about 10-30 weight percent of elementary iodine; and
   II. about 90-70 weight percent of at least one polycarboxylate having an average degree of polymerization (numerical average value) between about 10 and 500, said polycarboxylate consisting essentially of:
   Y + W/2 basic mole % units of the formula

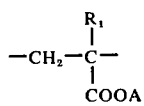

(I)

U — W basic mole % units of the formula

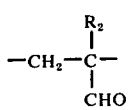

(II)

Z basic mole % units of the formula

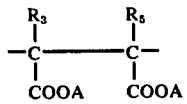

(III)

W/2 basic mole % units of the formula

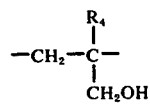

(IV)

V basic mole % units of the formula

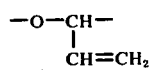

(V)

wherein U equals about 5-30; V equals about 1-25; W equals 0 to U; Y equals 100 − (U + V + Z); and Z equals 0 to 20; A represents an alkali metal or hydrogen ion; $R_1$ signifies hydrogen, methyl, hydroxy methyl, ethyl, chlorine or bromine; $R_2$ and $R_4$ are the same or different and signify hydrogen or hydroxymethyl; $R_3$ and $R_5$ are the same or different and signify hydrogen, methyl or ethyl; and whereby the expression Y + (W/2) + 2Z is larger than or equal to about 65;

b. about 0-20 weight percent of at least one alkali metal iodide, ammonium iodide, mixtures of said iodides or at least one lower, monovalent, aliphatic alcohol;

c. about 0-20 weight percent of at least one acid selected from the group consisting of sulfuric acid, phosphoric acid, citric acid, malic acid and tartaric acid; and d. water in an amount sufficient so that said aqueous solution comprises 100 weight percent;

wherein said heating is conducted at between about 50° and 120° C for about 0.75 to 15 hours to form said iodophor.

16. Iodophor according to claim 15 wherein said polycarboxylate has an average degree of polymerization of about 10-300.

17. Iodophor according to claim 16 wherein said average degree of polymerization is about 15-100.

18. Iodophor according to claim 15 wherein V equals about 1-15; W equals 0 to about 0.3 U; Z equals 0 to about 10; A represents a hydrogen ion; $R_1$ and Ru hydrogen or hydroxy methyl; $R_2$, $R_3$ and $R_5$ are each hydrogen.

19. Iodophor according to claim 18 wherein V equals about 1-10; W equals 0; Z equals 0; and $R_1$ signifies hydrogen.

20. Iodophor according to claim 18 wherein said alkali metal iodide is sodium iodide.

21. Iodophor according to claim 18 wherein said alcohol is a $C_1$-$C_3$ saturated, monovalent, aliphatic alcohol.

22. Iodophor according to claim 15 having a content of about 7-26 weight percent active iodine.

23. Iodophor according to claim 15 having a weight ratio of active iodine to inactive iodine therein between about 16:1 and about 2:1.

* * * * *